United States Patent
Dong

(10) Patent No.: US 9,934,419 B2
(45) Date of Patent: Apr. 3, 2018

(54) PACKAGE STRUCTURE, ELECTRONIC DEVICE AND METHOD FOR MANUFACTURING PACKAGE STRUCTURE

(71) Applicant: Shenzhen Goodix Technology Co., Ltd., Shenzhen (CN)

(72) Inventor: Haoxiang Dong, Shenzhen (CN)

(73) Assignee: Shenzhen Goodix Technology Co., Ltd., Shenzhen (CN)

( * ) Notice: Subject to any disclaimer, the term of this patent is extended or adjusted under 35 U.S.C. 154(b) by 0 days.

(21) Appl. No.: 15/477,084

(22) Filed: Apr. 1, 2017

(65) Prior Publication Data

US 2017/0243049 A1    Aug. 24, 2017

Related U.S. Application Data

(63) Continuation of application No. PCT/CN2016/089356, filed on Jul. 8, 2016.

(30) Foreign Application Priority Data

Feb. 23, 2016  (CN) .......................... 2016 1 0100363

(51) Int. Cl.
*H05K 7/00* (2006.01)
*G06K 9/00* (2006.01)
(Continued)

(52) U.S. Cl.
CPC ...... *G06K 9/00053* (2013.01); *A61B 5/02416* (2013.01); *A61B 5/0531* (2013.01);
(Continued)

(58) Field of Classification Search
CPC ............ A61B 2562/04; A61B 2562/12; A61B 2562/166; A61B 2562/242;
(Continued)

(56) References Cited

U.S. PATENT DOCUMENTS 6,747,345 B1 *  6/2004  Bolken ................. H01L 21/565
                                                    257/678
8,537,124 B2    9/2013  Lee et al.
(Continued)

FOREIGN PATENT DOCUMENTS

CN       101587400 A    11/2009
CN       203858644 U    10/2014
(Continued)

OTHER PUBLICATIONS

International Search Report for International Application No. PCT/CN2016/089356, Applicant: Shenzhen Huiding Technology Co., Ltd., Nov. 29, 2016, 5 pages.

*Primary Examiner* — Yuriy Semenenko

(57) ABSTRACT

A package structure, an electronic device and a method for manufacturing the package structure are presented. The package structure comprises: a substrate (100), a sensing module (200) disposed on an upper surface of the substrate (100) and electrically connected to the substrate (100), and a package colloid (300) disposed on the upper surface of the substrate (100) and coating at least one portion of the sensing module (200), wherein the sensing module (200) comprises a capacitive sensor (210) and an optical sensor (220), and the package colloid (300) comprises at least one portion of a photic zone (310) disposed corresponding to the optical sensor (220). Thus, the capacitive sensor and the optical sensor can be packaged in one package structure, so as to improve the degree of integration of the package structure and save the package space.

11 Claims, 3 Drawing Sheets

(51) Int. Cl.

| | |
|---|---|
| *H01L 31/0203* | (2014.01) |
| *H05K 3/28* | (2006.01) |
| *H05K 3/06* | (2006.01) |
| *H01L 31/18* | (2006.01) |
| *H01L 27/146* | (2006.01) |
| *A61B 5/024* | (2006.01) |
| *A61B 5/053* | (2006.01) |
| *A61B 5/1455* | (2006.01) |
| *A61B 5/1172* | (2016.01) |

(52) U.S. Cl.
CPC ........ *A61B 5/14551* (2013.01); *G06K 9/0002* (2013.01); *G06K 9/00114* (2013.01); *H01L 27/14618* (2013.01); *H01L 31/0203* (2013.01); *H01L 31/18* (2013.01); *H05K 3/067* (2013.01); *H05K 3/284* (2013.01); *A61B 5/1172* (2013.01); *A61B 2562/04* (2013.01); *A61B 2562/12* (2013.01); *A61B 2562/166* (2013.01); *A61B 2562/242* (2013.01); *A61B 2562/247* (2013.01); *H01L 2924/15* (2013.01); *H05K 2201/09818* (2013.01)

(58) Field of Classification Search
CPC .......... A61B 2562/247; A61B 5/02416; A61B 5/0531; A61B 5/1172; A61B 5/14551; G06K 9/0002; G06K 9/00053; G06K 9/00114; H01L 27/14618
See application file for complete search history.

(56) References Cited

U.S. PATENT DOCUMENTS

| | | | |
|---|---|---|---|
| 8,779,443 B2* | 7/2014 | Wong | H01L 25/167 257/84 |
| 9,727,770 B2* | 8/2017 | Gozzini | G06K 9/0002 |
| 2003/0148556 A1* | 8/2003 | Zhou | H01L 21/565 438/127 |
| 2010/0039406 A1 | 2/2010 | Lee et al. | |
| 2010/0187557 A1* | 7/2010 | Samoilov | H01L 27/144 257/99 |
| 2013/0164867 A1* | 6/2013 | Ramasamy | H01L 27/14618 438/25 |
| 2013/0248887 A1* | 9/2013 | Coffy | G01S 7/481 257/81 |
| 2014/0231635 A1* | 8/2014 | Kerness | G01S 17/026 250/226 |
| 2015/0233738 A1* | 8/2015 | Vokinger | G01D 5/34746 250/231.1 |
| 2016/0041029 A1 | 2/2016 | T'Ng et al. | |
| 2017/0229425 A1* | 8/2017 | Chang | H01L 21/565 |
| 2017/0271175 A1* | 9/2017 | Healy | H01L 21/563 |
| 2017/0287865 A1* | 10/2017 | Yu | H01L 24/16 |
| 2017/0287886 A1* | 10/2017 | Gani | H01S 5/02248 |

FOREIGN PATENT DOCUMENTS

| | | |
|---|---|---|
| CN | 203982403 U | 12/2014 |
| TW | 201607013 A | 2/2016 |

\* cited by examiner

PACKAGE STRUCTURE, ELECTRONIC DEVICE AND METHOD FOR MANUFACTURING PACKAGE STRUCTURE

CROSS-REFERENCE TO RELATED APPLICATIONS

This application is a continuation of PCT Application No. PCT/CN2016/089356, filed on Jul. 8, 2016, which claims priority to Chinese Patent Application No. 201610100363.1, filed on Feb. 23, 2016. The disclosures of the aforementioned applications are hereby incorporated by reference in their entireties.

TECHNICAL FIELD

The present disclosure relates to the field of electronic technologies, and in particular, to a package structure, an electronic device, and a method for manufacturing the package structure.

BACKGROUND

With the increasing development of science and technology, people's demand for mobile phones and new wearable electronic devices becomes higher and higher, and the aforementioned electronic devices are gradually developed towards multi-functions and miniaturization. The fingerprint identification technology as well as the heartbeat detection, the blood testing and other health indicator detection functions will also gradually become the standard configuration of mobile phones and wearable electronic products. Since lightweight, thinness and miniaturization is a major trend in the current consumer electronic development, how to realize more functions in an increasingly smaller volume of a chip becomes one of the major problems to be addressed by the current chip design and the package technology.

However, the current package structure and the package method still need to be improved.

SUMMARY

The present application is made based on the findings and understandings regarding the following facts and problems by the inventor:

In one aspect of the present disclosure, the present disclosure presents a package structure; according to an embodiment of the present disclosure, the package structure includes: a substrate; a sensing module disposed on an upper surface of the substrate and electrically connected to the substrate; and a package colloid disposed on the upper surface of the substrate and coating at least one portion of the sensing module, where the sensing module includes a capacitive sensor and an optical sensor, and the package colloid includes at least one portion of a photic zone disposed corresponding to the optical sensor. Thus, the capacitive sensor and the optical sensor can be packaged in one package structure, so as to improve the degree of integration of the package structure and save the package space.

In another aspect of the present disclosure, the present disclosure presents an electronic device. According to an embodiment of the present disclosure, the electronic device includes the previously described package structure. Thus, part of functions of the electronic device can be realized through the previously described package structure with simple manufacture and high degree of integration, so as to save space in the electronic device and reduce the volume of the electronic device.

In another aspect of the present disclosure, the present application presents a method for manufacturing the package structure described previously. According to an embodiment of the present disclosure, the method includes: (1) a sensing module disposed on an upper surface of a substrate, to electrically connected to the substrate, where the sensing module includes a capacitive sensor and an optical sensor; and (2) a package colloid disposed on the upper surface of the substrate, coating at least one portion of the sensing module, and including a photic zone, where at least one portion of the photic zone is disposed corresponding to the optical sensor. Thus, the capacitive sensor and the optical sensor can be simply packaged in a same package structure, so as to improve the degree of integration of the package structure manufactured by the method.

DESCRIPTION OF EMBODIMENTS

Embodiments of the present disclosure are described in details below, and examples of the embodiments are shown in the accompanying drawings. The embodiments described below with reference to the drawings are exemplary, intend for explaining the present disclosure and should not be understood as limitation to the present disclosure.

Figure 1:
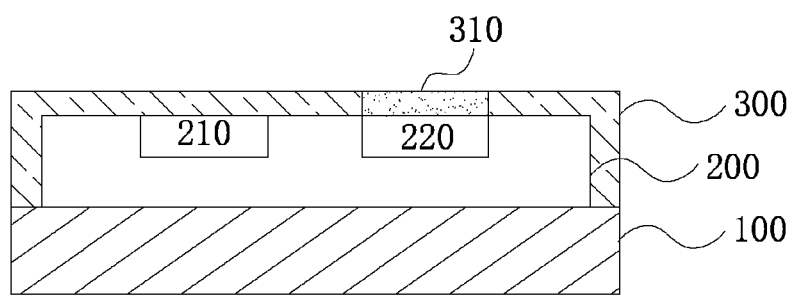
FIG. 1 illustrates a structural schematic diagram of a package structure according to an embodiment of the present disclosure.

According to an embodiment of the present disclosure and referring to FIG. 1, the package structure includes: a substrate 100, a sensing module 200 and a package colloid 300. In particular, the sensing module 200 is disposed on an upper surface of the substrate 100 and electrically connected to the substrate 100. The package colloid 300 is disposed on the upper surface of the substrate 100 and coating at least one portion of the sensing module 200. The sensing module 200 includes a capacitive sensor 210 and an optical sensor 220, and the package colloid 300 includes at least one portion of a photic zone 310 disposed corresponding to the optical sensor 220; that is to say, the photic zone 310 is disposed above or around the optical sensor 220, and at least one portion of the photic zone 310 is disposed above or around the optical sensor 220, so that the optical sensor 220 can receive refracted or scattered light signal, to achieve the optical sensing function. Thus, the uniform package of the capacitive sensor 210 and the optical sensor 220 in the same package structure can be realized, to improve the degree of integration of the package structure, simplify the manufacture of the package structure including the optical sensing and capacitive sensing functions, save space and reduce costs.

A detailed description of each part of the package structure will be given below.

According to an embodiment of the present disclosure, the substrate 100 can be a printed circuit board, including a circuit, so that the sensing module 200 can be connected to the circuit in the substrate 100 via a bonding wire or the like, to introduce a sensing signal to the substrate; the substrate is then interconnected to the external signal via a terminal, a solder ball or the like, to achieve the use function of the package structure. It should be noted that, the specific implementation manner of the electric connection between the sensing module 200 and the substrate 100 is not particularly limited; those of ordinary skill in the art in the art can design the specific implementation manner of the electric connection according to the specific structure and positional relationship of each component in the package structure, as long as the capacitive sensing signal and the optical sensing signal in the sensing module 200 can be output via the substrate 100. For example, according to an embodiment of the present disclosure and referring to FIG. 3, the electric connection between the sensing module 200 and the substrate 100 can be achieved using a metal wire. According to another embodiment of the present disclosure, the internal signal of the package structure can be connected to the external via a terminal formed by a substrate connecting finger which is disposed on a lower surface of the substrate 100, for example, formed of the gold-plated copper, with one end connected to the circuit in the substrate and the other end interconnected to the reflow pad signal.

The sensing module 200 includes a capacitive sensor 210 and an optical sensor 220. In particular, the optical signal is reflected and refracted after it comes into contact with a measured object (such as a user's finger), and this portion of the reflected or refracted optical signal is received by the optical sensor. As the intensity of the reflected or refracted optical signal changes with a series of changes such as the heartbeat and the blood oxygen of human body, the optical sensor 220 can obtain a series of data such as the heartbeat and the blood oxygen of human body by capturing the changes of the intensity of optical signal followed by a series of calculations. Meanwhile, when the measured object (the finger) presses above the package structure, a capacitor can be formed along with the capacitive sensor below. Due to the existence of gullies in the fingerprint of human finger, the capacitor formed by the finger and the capacitive sensor has different capacitances in the crest and trough of the fingerprint, while fingerprint information of the finger can be obtained by detecting such different capacitances through the capacitive sensor. After the intensive study, the inventor finds that many of current optical sensors are pressed to use for the finger zone due to the dense capillary of the finger which is convenient for the optical sensor to collect the signal. However, for the fingerprint identification, the fingerprint collected is also in the finger zone, thereby there is an overlap between two positions, a multiple-zone press can be converted into a single-zone press by integrating two sensors, and two types of information, i.e., fingerprint information and optical information, can be collected at the same time, which attributes to improving the user experience. Therefore, the present disclosure can effectively enhance the integration degree of the package structure with occupying a smaller volume to achieve the same function by an integrated package of the capacitive sensor 210 and the optical sensor 220; meanwhile, a plurality of package structures are replaced with one package structure in favor of reducing the cost of the raw material and the package.

Figure 2:
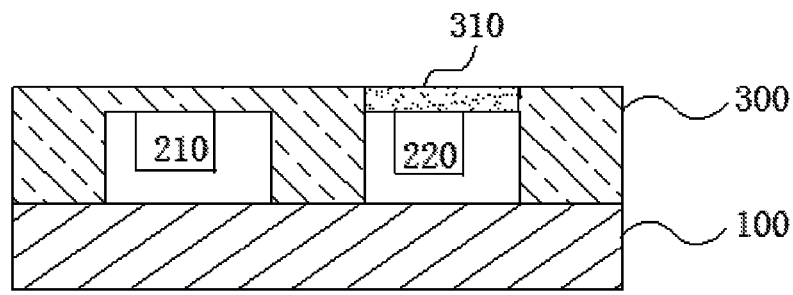
FIG. 2 illustrates a structural schematic diagram of a package structure according to another embodiment of the present disclosure.

According to an embodiment of the present disclosure and referring to FIG. 1, the sensing module 200 can be a chip that integrates a capacitive sensing function with an optical sensing function. According to another embodiment of the present disclosure and referring to FIG. 2, the sensing module 200 can further be two chips having a single function of the capacitive sensing function and the optical sensing function, respectively. Therefore, the processing of the capacitive sensing signal and the optical sensing signal can be achieved respectively using two chips having a single function.

Those of ordinary skill in the art may understand that in order to achieve the processing and output of the sensing signal, the sensing module 200 can further possess a metal bonding plate electrically connected to the substrate 100 using a bonding wire, so as to achieve the communication between the sensing module 200 and the substrate 100.

According to an embodiment of the present disclosure, the package colloid 300 is disposed on the upper surface of the substrate 100, and coating at least one portion of the sensing module 200. In particular, the package colloid 300 can be formed by the package adhesive and molded by the manner of molding or the like, so that each component in the package structure can be moved as a whole or subjected to various types of connection operations. Moreover, the package colloid 300 can further play a role in protecting the sensing module 200 and connection lines connecting the sensing module 200 to the bonding wire of the substrate 100 from being damaged during use. Besides, the package colloid 300 can provide an excellent electrical and optical sensing environment for the capacitive sensor and the optical sensor, and dissipate heat simultaneously, so as to improve the actual use effect of the sensing module 200.

In particular, the package colloid 300 includes a photic zone 310 disposed corresponding to the optical sensor 220. As previously mentioned, the optical sensor 220 needs to receive the refracted light or the scattered light to realize the sensing function in the process of the actual use, thus, the photic zone 310 is disposed at a position corresponding to the optical sensor 220, that is, a position above and around the optical sensor 220 which needs to receive the light, so that the refracted light or scattered light can pass through the photic zone 310 to be received by the optical sensor 220. According to an embodiment of the present disclosure, the photic zone 310 is made of a transparent material. Those of ordinary skill in the art may understand that in the present disclosure, the term "transparent material" should be comprehended in a broad sense. That is, the light with sufficient intensity can pass through the photic zone 310 made of the transparent material to be received by the optical sensor 220 disposed below the photic zone 310, to realize the sensing function of the optical sensor 220. In particular, according to an embodiment of the present disclosure, the aforementioned "transparent material" can be the material having a transmittance of not less than 20%. For example, the photic zone 310 can be formed using transparent glue or glass.

It should be noted that, the specific configuration and the setting manner of the aforementioned package colloid 300 are not particularly limited, as long as the capacitive sensor 210 and the optical sensor 220 can be normally operated, the package of the package structure can be realized, and the structure such as the sensing module 200 and the bonding wire can be protected. For example, according to an embodiment of the present disclosure, the package colloid 300 can be made of a transparent material. Thus, the package colloid 300 can be formed simply by integrally molding.

According to an embodiment of the present disclosure, the specific setting manner of the photic zone 310 is not particularly limited; those of ordinary skill in the art can design according to the specific condition of the package structure. For example, according to some embodiments of the present disclosure, the photic zone 310 is disposed at a position corresponding to the optical sensor 220 by a liquid material such as transparent glue or the like, adopting but not limited to the manner of stencil printing or spin-coating, and then other portions of the package colloid 300 are formed by an opaque material (i.e., the material having a light transmittance of less than 20%), so as to protect the package structure. According to other embodiments of the present disclosure, the photic zone 310 can also be disposed at a position corresponding to the optical sensor 220 by the manner of dispensing or the like. Besides, the photic zone 310 can further be disposed at a position corresponding to the optical sensor 220 by special-shaped mold molding, and then other portions of the package colloid 300 are formed by the mold matched thereto. Alternatively, other portions of the package colloid 300 can also be disposed using an opaque material at a position other than the corresponding position of the optical sensor 220 by special-shaped molds, and then the photic zone 310 is formed by using the matched molds.

Figure 4:
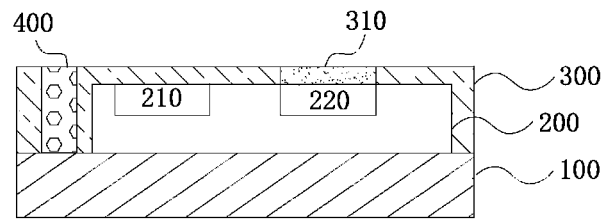
FIG. 4 illustrates a structural schematic diagram of part of a package structure according to a further embodiment of the present disclosure.

According to an embodiment of the present disclosure, in order to improve the sensing effect of the optical sensor and further enhance the degree of integration of the package structure according to an embodiment of the present disclosure, referring to FIG. 4, the package structure can further include an LED module 400. In particular, the LED module can provide a stable backlight light source for the optical sensor 220, so that the optical sensor 220 can analyze and calculate the light signal refracted or reflected by the human hand based on parameters such as the light intensity of the light source, and the human's health parameters (the heartbeat, the blood pressure, the blood oxygen concentration, etc.) can be determined more accurately based on the aforementioned refracted or reflected light signal. The specific configuration of the LED module 400 and the specific light emission parameters of the backlight light source are not particularly limited; those of ordinary skill in the art can design the aforementioned parameters according to the actual condition. For example, the LED module 400 can emit a green light, a red light, or an infrared light as a backlight light source of the optical sensor 220.

To sum up, the package structure according to embodiments of the present disclosure is simple in manufacture, low in cost and high in chip integration degree. Thus, the simultaneous acquisition of the optical sensing signal and the capacitive sensing signal can be realized by pressing at the same position by the user's finger, thereby obtaining the user's fingerprint information and realizing the health monitoring. The package structure according to embodiments of the present disclosure can save space and facilitate reducing the volume of the package structure.

In another aspect of the present disclosure, the present disclosure presents an electronic device. In particular, according to an embodiment of the present disclosure, the electronic device includes the previously described package structure. Thus, the simultaneous acquisition of an optical sensing signal and a capacitive sensing signal can be realized by pressing at the same position by a user's finger, thereby obtaining the user's fingerprint information and realizing the health monitoring, Part of functions of the electronic device are realized by using the previously described package structure with simple manufacture, low cost and high degree of integration, so as to save space of the electronic device and reduce the volume of the electronic device.

In particular, according to an embodiment of the present disclosure, the electronic device can further include a flex board and a mainboard. The flex board is electrically connected to the package structure, as well as the mainboard is electrically connected to the flex board and adapted to controlling the electronic device based on the sensing signal of the sensing module in the package structure. It should be noted that, the specific manner of the electrical connection between the package structure and the flex board as well as the flex board and the mainboard is not particularly limited; for example, according to a specific embodiment of the present disclosure, the solder ball can be disposed on a lower surface of the substrate via a package manner of a Ball Grid Array (Ball Grid Array, BGA), and the substrate is connected to the flex board by the reflow. According to another embodiment of the present disclosure, the electrical connection between the substrate and the flex board can be realized via a package manner of a Land Grid Array (Land Grid Array, LGA). The flex board is further electrically connected to the mainboard; thus, the sensing signal received from the package structure can be output to the mainboard, and the mainboard can realize the control of the electronic device based on the aforementioned signal. Therefore, the relevant control of the electronic device can be simply realized by using the sensing signal emitted from the sensing element in the package structure, so as to extend the use function of the electronic device.

In another aspect of the present disclosure, the present disclosure presents a method for manufacturing the package structure described previously. According to an embodiment of the present disclosure, the method includes:

S100 dispose a sensing module

According to an embodiment of the present disclosure, in the step, a sensing module is disposed on the upper surface of a substrate. The specific type of the substrate is described in detail previously, and will not be described redundantly herein. For example, the substrate includes a circuit, so that the sensing module can be connected to the circuit in the substrate to introduce a sensing signal to the substrate, and the substrate is then interconnected to the external signal via a terminal, a solder ball or the like, so as to achieve the use function of the package structure. In particular, the sensing module includes a capacitive sensor and an optical sensor; in the step, the sensing module containing the aforementioned element is disposed on the upper surface of the substrate and electrically connected to the substrate. The specific configuration of the sensing module is described in detail previously, and will not be described redundantly herein.

In particular, according to an embodiment of the present disclosure, the sensing module 200 can be fixed on the upper surface of the substrate using a DAF Film (Die Attach Film, DAF), an epoxy resin or other thermosetting polymers as well as a material having an adhesive function such as glue. Thus, the capacitive sensor and the optical sensor can be simply fixed on the substrate, so as to realize the actual use function of the package structure.

Furthermore, in order to further enhance the degree of integration of the package structure manufactured by the method and improve the use effect of the optical sensor, before disposing the sensing module, the method can further include:

S10 dispose an LED module

According to an embodiment of the present disclosure, in the step, an LED module is disposed on the upper surface of the substrate. In particular, the LED module is disposed on the upper surface of the substrate, so that the LED module can be used to provide a stable backlight light source for the optical sensor; accordingly, the optical sensor can analyze and calculate the light signal refracted or reflected by the human hand based on parameters such as the light intensity of the light source, and the human's health parameters (the heartbeat, the blood pressure, the blood oxygen concentration, etc.) can be determined more accurately based on the aforementioned refractive or reflective light signal. The specific structure of the LED module is described in detail previously, and will not be described redundantly herein. In particular, in the step, the packaged LED module can be disposed on the upper surface of the substrate through the surface mounted technology; further, an LED chip can be bonded to the substrate and electrically connected to the substrate by a bonding wire, a manner of dispensing, but not limited to dispensing is then adopted, and the LED module is formed using the transparent plastic sealant to perform the dispensing only above and around the LED chip. Those of ordinary skill in the art may understand that in the package structure according to an embodiment of the present disclosure, the light can pass through a zone corresponding to the upper surface of the LED module, so that the light emitted by the LED module can pass through this portion of the zone, thereby ensuring that the light can be received by the optical sensor after the reflection or the refraction. In order to further improve the backlight effect provided by the LED module, in this step, the zone corresponding to the upper surface of the LED module can be further polished, so as to make a thin package colloid which is beneficial to emit the backlight.

S200 dispose a package colloid

According to an embodiment of the present disclosure, in the step, a package colloid is disposed on the upper surface of the substrate, coating at least one portion of the sensing module, and including a photic zone, where the photic zone is disposed corresponding to the optical sensor. Thus, the capacitive sensor and the optical sensor can be simply packaged in one package structure, so as to improve the degree of integration of the package structure manufactured by the method. Those of ordinary skill in the art may understand that before disposing the package colloid, the method can further include, but not limited to, the relevant processing steps in the traditional package flow, such as the steps of wafer grinding, sawing, patching, as well as disposing a bonding pad, soldering wires and soldering balls.

As previously mentioned, the optical sensor needs to receive the refracted light or the scattered light to realize the sensing function in the process of the actual use. Therefore, the photic zone is disposed at a position corresponding to the optical sensor, i.e., the photic zone is disposed at a position above the optical sensor where light is to be received, so that the refracted light or scattered light can pass through the photic zone to be received by the optical sensor. The material forming the photic zone is described in detail previously, and will not be described redundantly herein.

It should be noted that, the specific configuration and the setting manner of the aforementioned package colloid and the photic zone are not particularly limited, as long as the capacitive sensor and the optical sensor can be normally operated, the package of the package structure can be realized, and the structure such as the sensing module and the bonding wire can be protected.

According to an embodiment of the present disclosure, the photic zone can be disposed by stencil printing, spin-coating and photoetching, special-shaped mold molding, dispensing or patching. Thus, the setting of the photic zone can be realized using the aforementioned manner which is simple in manufacture, low in cost and easy for large scale production. According to another embodiment of the present disclosure, the package colloid can be made of a transparent material, and integrally formed on the upper surface of the substrate. Thus, the use function of the optical sensor can be realized simply through an integral package.

It should be noted that, the specific setting manner of the photic zone or the package colloid is not particularly limited; those of ordinary skill in the art can design according to the specific condition of the package structure. For example, according to some embodiments of the present disclosure, the photic zone is disposed at a position corresponding to the optical sensor by a liquid materials such as transparent glue or the like, adopting but not limited to the manner of stencil printing or spin-coating, and then other portions of the package colloid are formed by an opaque material (i.e., the material having a light transmittance of less than 20%), so as to protect the package structure. According to other embodiments of the present disclosure, the photic zone can also be disposed at a position corresponding to the optical sensor by the manner of dispensing or the like. Besides, the photic zone can further be disposed at a position corresponding to the optical sensor by special-shaped mold molding, and then other portions of the package colloid are formed by the molds matched thereto. Alternatively, other portions of the package colloid can also be disposed using an opaque material at a position other than the corresponding position of the optical sensor by special-shaped molds, and then the photic zone is formed by using the matched mold.

In particular, according to an embodiment of the present disclosure, the setting of the package colloid can be realized using a transparent package colloid through an integral molding, and then the photic zone of the corresponding zone of the optical sensor is made thin by adopting the manner of polishing or the like, enabling the light to pass through the photic zone, so as to realize the manufacture of the package structure. According to an embodiment of the present disclosure, in order to reduce a signal-to-noise ratio of the optical sensor and expel from the disturbance of the external light source, the photic zone can be further disposed on the upper surface of the optical sensor using the transparent glue or the like by stencil printing, spin-coating and photoetching, special-shaped injection mold molding, dispensing or the like; the photic zone can also be formed by disposing a thin film formed by transparent glass or transparent glue on the upper surface of the optical sensor via a patch technology. That is to say, the photic zone is only disposed corresponding to the optical sensor. According to an embodiment of the present disclosure, after forming the photic zone, the manufacture of the package structure can be further completed by entirely coating zones other than the photic zone using an opaque material and adopting but not limited to an Exposed Die Molding process; after disposing the photic zone, an opaque package colloid is disposed on the upper surface of the substrate via a plastic package process, to coat the sensing module, and then a surface of the opaque package colloid is polished to expose the photic zone.

Those of ordinary skill in the art may understand that the order of the aforementioned manufacture steps is not particularly limited as long as the manufactured package structure can be used to realize the use functions previously described. For example, according to an embodiment of the present disclosure, a portion of package colloid can be formed on the upper surface of the substrate using an opaque material by the manner of, but not limited to, special-shaped injection mold molding, and then the photic zone is disposed on the upper surface of the optical sensor. Alternatively, according to another embodiment of the present disclosure, the package structure according to embodiments of the present disclosure can be finally obtained by packaging the upper surface of the optical sensor and the capacitive sensor using the transparent material and then packaging other zones of the upper surface of the substrate using the opaque material.

To sum up, the manufacture method according to embodiments of the present disclosure has the advantages of simple steps, low cost and high integration degree of the manufactured package structure. Thus, the simultaneous acquisition of the optical sensing signal and the capacitive sensing signal can be realized by pressing at the same position by the user's finger, thereby obtaining the user's fingerprint information and realizing the health monitoring. The package structure manufactured by the method according to embodiments of the present disclosure can save space and facilitate reducing the volume of the package structure.

The solutions of the present disclosure will be explained in combination with embodiments. Those of ordinary skill in the art may understand that the following embodiments are merely used for explaining the present disclosure, rather than regarding as a limitation of the scope of the present disclosure. Embodiments with no specific techniques or conditions specified are conducted according to techniques or conditions described in the literature in the art or according to the product specification. Used reagents or instruments with no manufacturers specified are all conventional products available to obtain commercially.

Embodiment 1 LED External Package

Figure 3:
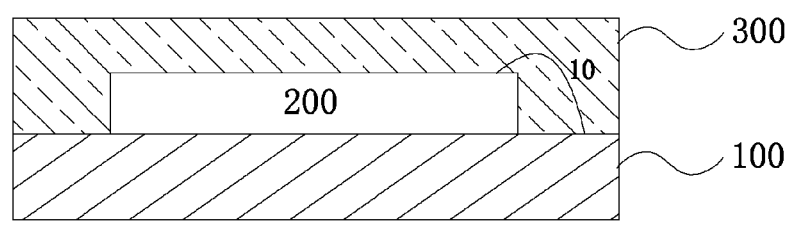
FIG. 3 illustrates a structural schematic diagram of part of a package structure according to a further embodiment of the present disclosure.

First, after wafer grinding, sawing, patching and soldering wires, the entire chip is plastic packaged using the transparent plastic sealant, to achieve a better transmittance of the package colloid above the optical sensor, thereby ensuring the optical sensor to achieve the function. Meanwhile, the thickness of the package colloid above the sensing module is controlled, to ensure that the function of the capacitive sensor is achieved. The manufactured package structure is shown in FIG. 3.

Embodiment 2 LED External Package

First, with the wafer level processing method, a transparent plastic package protective layer is pre-generated on the surface of the optical sensor by using the manner of metal stencil printing, a series of crafts such as wafer grinding, sawing, patching and soldering wires is performed, and then the opaque plastic sealant is used to perform an Exposed Die Molding (Exposed Die Molding) package, to ensure that the generated transparent plastic package protective layer is exposed, so as to guarantee that the function of the optical sensor is achieved. Meanwhile, the thickness of the package colloid above the sensing module is controlled, to ensure that the function of the capacitive sensor is achieved. The manufactured package structure is shown in FIG. 1.

Embodiment 3 LED External Package

First, with the wafer level processing method, a transparent plastic package protective layer is pre-generated on the surface of the optical sensor by using the manner of spin-coating and photoetching, a series of crafts such as wafer grinding, sawing, patching and soldering wires is performed, and then the opaque plastic sealant is used to perform an Exposed Die Molding (Exposed Die Molding) package, to ensure that the generated transparent plastic package protective layer is exposed, so as to guarantee that the function of the optical sensor is achieved. Meanwhile, the thickness of the package colloid above the sensing module is controlled, to ensure that the function of the capacitive sensor is achieved. The manufactured package structure is shown in FIG. 1

Embodiment 4 LED External Package

Figure 5:
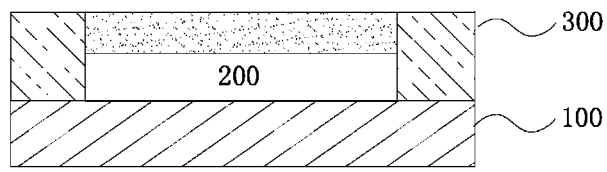
FIG. 5 illustrates a structural schematic diagram of part of a package structure according to a further embodiment of the present disclosure.

First, with the wafer level processing method, a transparent plastic package protective layer is pre-generated on the surface of the sensing module by using the manner of spin-coating and photoetching, a series of crafts such as wafer grinding, sawing, patching and soldering wires is performed, and then the opaque plastic sealant is used to perform an Exposed Die Molding (Exposed Die Molding) package, to ensure that the generated transparent plastic package protective layer is exposed, so as to guarantee that the function of the optical sensor is achieved. Meanwhile, the thickness of the package colloid above the sensing module is controlled, to ensure that the function of the capacitive sensor is achieved. The manufactured package structure is shown in FIG. 5.

Embodiment 5 LED External Package

First, with the wafer level processing method, a transparent plastic package protective layer is pre-generated on the surface of the sensing module by using the manner of metal stencil printing, a series of crafts such as wafer grinding, sawing, patching and soldering wires is performed, and then the opaque plastic sealant is used to perform an Exposed Die Molding (Exposed Die Molding) package, to ensure that the generated transparent plastic package protective layer is exposed, so as to guarantee that the function of the optical sensor is achieved. Meanwhile, the thickness of the package colloid above the sensing module is controlled, to ensure that the function of the capacitive sensor is achieved. The manufactured package structure is shown in FIG. 5.

Embodiment 6 LED External Package

Figure 8:
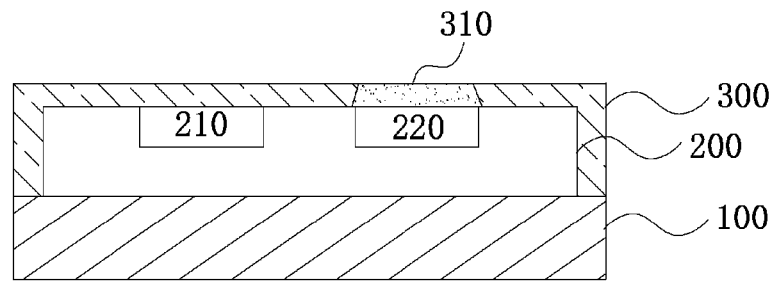
FIG. 8 illustrates a structural schematic diagram of part of a package structure according to a further embodiment of the present disclosure.

First, wafer grinding, sawing, patching and soldering wires are performed, then with the special-shaped injection mold, the first plastic package is performed only above and around the optical sensor by using the transparent plastic sealant; then the second plastic package is performed on other portions by reusing the matched injection mold and the opaque plastic sealant, for the plastic package and the protection of other portions, to ensure that the plastic sealant of the first plastic package is exposed, so as to guarantee that the function of the optical sensor is achieved. Meanwhile, the thickness of the package colloid above the sensing module is controlled, to ensure that the function of the capacitive sensor is achieved. The first plastic package can be conducted both after and before soldering wires. The manufactured package structure is shown in FIG. 8.

Embodiment 7 LED External Package

Figure 6:
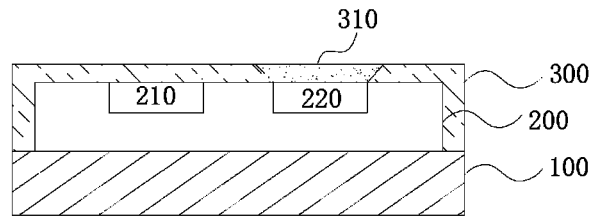
FIG. 6 illustrates a structural schematic diagram of part of a package structure according to a further embodiment of the present disclosure.

First, wafer grinding, sawing, patching and soldering wires are performed, then with the special-shaped injection mold, the first plastic package is performed on all space other than the top of the optical sensor by the opaque plastic sealant; then the second plastic package or no direct plastic package is performed above the optical sensor by reusing the matched injection mold and the transparent plastic sealant, to maintain that the top of the optical sensor is exposed, so as to guarantee that the function of the optical sensor is achieved. Meanwhile, the thickness of the package colloid above the sensing module is controlled, to ensure that the function of the capacitive sensor is achieved. The manufactured package structure is shown in FIG. 6.

Embodiment 8 LED External Package

First, wafer grinding, sawing, patching and soldering wires are performed, then a piece of transparent thin glass is pasted above the optical sensor by using transparent glue or a transparent film in a manner of patching, and the piece of glass needs to completely coat the optical sensor. Finally, other portions are plastic packaged by using the Exposed Die Molding process with an opaque plastic sealant. Meanwhile, the thickness of the structure such as the package colloid above the sensing module or the glass is controlled, to ensure that the function of the capacitive sensor is achieved. Pasting the transparent glass can be conducted both after and before soldering wires. The manufactured package structure is shown in FIG. 1.

Embodiment 9 LED External Package

First, wafer grinding, sawing, patching and soldering wires are performed, and then a piece of transparent thin glass is pasted above the sensing module by using transparent glue in a manner of patching. Finally, other portions are package by using the Exposed Die Molding process with an opaque plastic sealant. Meanwhile, the thickness of the structure such as the package colloid above the sensing module or the glass is controlled, to ensure that the function of the capacitive sensor is achieved. Pasting the transparent glass can be conducted both after and before soldering wire. The manufactured package structure is shown in FIG. 5.

The plastic package manner of embodiment 8 and embodiment 9 can further be packaging the entirety by using the opaque plastic sealant, and finally exposing the piece of thin glass by using, but not limited to, the manner of polishing the surface of the plastic package body. The piece of thin glass above the sensing module is made thin, to ensure that the function of the optical sensor is achieved.

Embodiment 10 LED External Package

First, with the wafer level processing method, an opaque plastic package protective layer is pre-generated on the portion of the package structure other than the surface of the sensing module or the portion of the surface of the sensing module other than the optical sensor by using the manner of metal stencil printing or spin-coating and photoetching, and other portions are plastic packaged by using the transparent plastic sealant through a series of package procedures of wafer grinding, sawing, patching, soldering wires, Exposed Die Molding and the like. Meanwhile, the thickness of the package colloid above the sensing module is controlled, to ensure that the function of the capacitive sensor is achieved. The manufactured package structure is shown in FIG. 1 or FIG. 5.

The plastic package manner of embodiments 2-5 and 10 can further be packaging the entirety by using the opaque plastic sealant, and finally exposing the transparent zone above the sensing module or the optical sensor by using, but not limited to, the manner of polishing the surface of the package colloid. Meanwhile, the thickness of the package colloid above the sensing module is controlled, to ensure that the function of the capacitive sensor is achieved.

Embodiment 11 LED External Package

Figure 7:
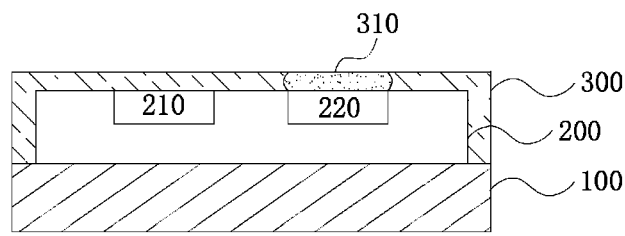
FIG. 7 illustrates a structural schematic diagram of part of a package structure according to a further embodiment of the present disclosure.

First, wafer grinding, sawing, patching and soldering wires are performed, then the transparent plastic sealant is used to perform dispensing only above and around the optical sensor with the manner of dispensing, and then the entirety is plastic packaged by reusing the opaque plastic sealant. Finally, the transparent dispensing zone above the optical sensor is exposed by using, but not limited to, the manner of polishing the surface of the package colloid. The package colloid above the sensing module is made thin, to ensure that the function of the capacitive sensor is achieved. The manufactured package structure is shown in FIG. 7.

Embodiment 12 LED External Package

Figure 9:
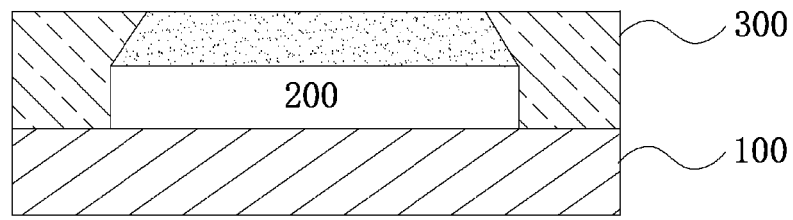
FIG. 9 illustrates a structural schematic diagram of part of a package structure according to a further embodiment of the present disclosure.

First, wafer grinding, sawing, patching and soldering wires are performed according to the traditional package flow, then with the special-shaped injection mold, the first plastic package is performed on the surface of the sensing module other than the position of the metal bonding pad by using the transparent plastic sealant; then the second plastic package is performed on other portions by reusing the matched injection mold and the opaque plastic sealant, for the plastic package and the protection of other portions, to ensure that the plastic sealant of the first plastic package is exposed, so as to guarantee that the function of the optical sensor is achieved at the same time. Meanwhile, the thickness of the package colloid above the sensing module is controlled, to ensure that the function of the capacitive sensor is achieved. The first plastic package can be conducted both after and before soldering wires. The manufactured package structure is shown in FIG. 9.

Embodiment 13 LED Internal Package

The packaged LED is first disposed on the substrate using the surface mounted technology, and then the subsequent package processing is performed in combination with the package solutions of embodiments 1-12. Meanwhile, the thickness of the package colloid above the sensing module is controlled, to ensure that the function of the capacitive sensor is achieved. The manufactured package structure is shown in FIG. 4.

Embodiment 14 LED Internal Package

Figure 10:
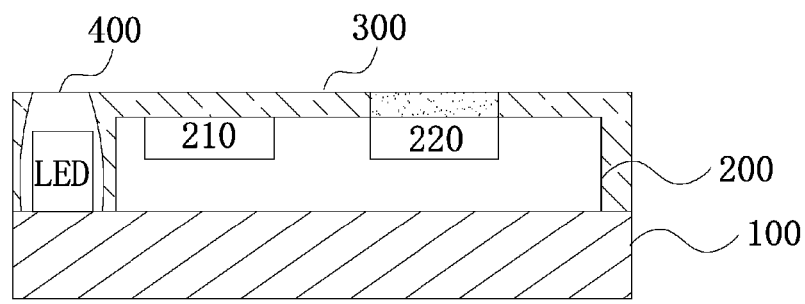
FIG. 10 illustrates a structural schematic diagram of part of a package structure according to a further embodiment of the present disclosure.

First, an LED bare chip is bonded to the substrate and soldering wires, then with the manner of dispensing, the transparent package sealant is used to perform dispensing only above and around the LED bare chip, then the subsequent package processing is performed in combination with the package solutions of embodiments 1-12, and finally the polishing process is performed on the surface of the package colloid, to expose the LED and the transparent zone above the optical sensor, so as to ensure that the function of the LED and the optical sensor are achieved. The package colloid above the sensing module is made thin, to ensure that the function of the capacitive sensor is achieved. The manufactured package structure is shown in FIG. 10.

In the description of the present disclosure, it should be understood that the orientation or positional relationship indicated by the terms "above", "below", "vertical", "horizontal", "top", "bottom" and the like is the orientation or positional relationship based on the accompanying drawings, which is merely for the purpose of facilitating the description of the present disclosure and simplifying the description, rather than indicating or implying that the device or the element referred to must be of a particular orientation, as well as constructed and operated in a particular orientation, and therefore should not be understood as limitation to the present disclosure.

In the present disclosure, unless otherwise specified and defined, the terms "install", "link", "connect", "fix" and the like should be understood in a broad sense; for example, they can be understood as a fixed connection or a detachable connection or an integrated connection ; they can be understood as a mechanical connection or an electrical connection, or they can be understood as communicating with each other; they can be understood as a direct connection, an indirectly connection through an intermediary, an internal connection between two elements or an interactive relationship between two elements. For those of ordinary skill in the art, the specific meanings of the aforementioned terms in the present disclosure can be understood according to the specific conditions.

In the present disclosure, unless otherwise specified and defined, the first feature "above" or "below" the second feature can be a direct contact between the first and second feature, or an indirect contact between the first and second feature though an intermediary. Besides, the first feature "above", "over" and "on" the second feature can be the first feature right above or obliquely above the second feature, or simply represent that the horizontal altitude of the first feature is higher than that of the second feature. The first feature "below", "under" and "underneath" the second feature can be the first feature right below or obliquely below the second feature, or simply represent that the horizontal altitude of the first feature is less than that of the second feature.

In the description of the present specification, the description of reference terms "an embodiment", "some embodiments", "examples", "specific examples", or "some examples" and the like refers to a particular feature, structure, material or characteristic described in combination with the embodiment or example included in at least one embodiment or example of the present disclosure. In the present specification, schematic expressions of the aforementioned terms do not have to be directed to the same embodiment or example. Moreover, the particular feature, structure, material, or characteristic described can be combined in a suitable manner in any one or more embodiments or examples. In addition, those of ordinary skill in the art can, in the absence of mutual contradictions, combine and group the different embodiments or examples and the features of different embodiments or examples described in the present specification.

Although embodiments of the present disclosure have been shown and described above, it can be understood that the above embodiments are exemplary and are not to be understood as a limitation to the present disclosure; those of ordinary skill in the art, within the scope of the present disclosure, can change, modify, substitute and vary the above embodiments.

What is claimed is:

1. A package structure, comprising:
   a substrate;
   a sensing module disposed on an upper surface of the substrate and electrically connected to the substrate; and
   a package colloid disposed on the upper surface of the substrate and coating at least one portion of the sensing module,
   wherein the sensing module comprises a capacitive sensor and an optical sensor, and
   the package colloid comprises at least one portion of a photic zone disposed corresponding to the optical sensor.

2. The package structure according to claim 1, wherein the photic zone is made of a transparent material.

3. The package structure according to claim 1, wherein the package colloid is made of a transparent material.

4. The package structure according to claim 1, further comprising an LED module disposed on the upper surface of the substrate.

5. An electronic device, comprising a package structure, wherein the package structure comprises:
   a substrate;
   a sensing module disposed on an upper surface of the substrate and electrically connected to the substrate; and
   a package colloid disposed on the upper surface of the substrate and coating at least one portion of the sensing module,
   wherein the sensing module comprises a capacitive sensor and an optical sensor, and
   the package colloid comprises at least one portion of a photic zone disposed corresponding to the optical sensor.

6. A method for manufacturing a package module, comprising:
   disposing a sensing module on an upper surface of a substrate, to electrically connected to the substrate, wherein the sensing module comprises a capacitive sensor and an optical sensor; and
   disposing a package colloid on the upper surface of the substrate, coating at least one portion of the sensing module, wherein the disposed package colloid comprises a photic zone and at least one portion of the photic zone is disposed corresponding to the optical sensor.

7. The method according to claim 6, wherein in step of disposing a package colloid on the upper surface of the substrate, the package colloid is integrally formed on the upper surface of the substrate and made of a transparent material.

8. The method according to claim 7, wherein the step of disposing a package colloid on the upper surface of the substrate further comprises, after disposing the photic zone, disposing an opaque package colloid on a zone of the upper surface of the substrate other than the photic zone via an Exposed Die Molding process.

9. The method according to claim 7, wherein the step of disposing a package colloid on the upper surface of the substrate further comprises, after disposing the photic zone, disposing an opaque package colloid on the upper surface of the substrate via a plastic package process, to coat the sensing module;

polishing a surface of the opaque package colloid to expose the photic zone.

10. The method according to claim 6, wherein in step of disposing a package colloid on the upper surface of the substrate, the photic zone is disposed by any one way of stencil printing, spin-coating, photoetching, special-shaped mold molding, dispensing and patching.

11. The method according to claim 6, further comprises:

before disposing the sensing module, disposing an LED module on the upper surface of the substrate.

* * * * *